(12) United States Patent
Graham et al.

(10) Patent No.: US 9,022,036 B2
(45) Date of Patent: May 5, 2015

(54) PATIENT VENTILATING AND ASPIRATING SYSTEM

(75) Inventors: Peter Kenneth Graham, Auckland (NZ); Deshitha Airawana Edirisuriya, Auckland (NZ); Dwayne John Scollay, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1429 days.

(21) Appl. No.: 10/599,352

(22) PCT Filed: Mar. 30, 2005

(86) PCT No.: PCT/NZ2005/000057
§ 371 (c)(1),
(2), (4) Date: Oct. 18, 2007

(87) PCT Pub. No.: WO2005/094925
PCT Pub. Date: Oct. 13, 2005

(65) Prior Publication Data
US 2008/0271741 A1    Nov. 6, 2008

(30) Foreign Application Priority Data

Mar. 31, 2004    (NZ) ........................................ 532101

(51) Int. Cl.
*A61M 16/00*    (2006.01)
*A61M 16/04*    (2006.01)
*A61M 16/08*    (2006.01)
*A61M 16/10*    (2006.01)

(52) U.S. Cl.
CPC ....... *A61M 16/0465* (2013.01); *A61M 16/0463* (2013.01); *A61M 16/08* (2013.01); *A61M 16/109* (2013.01)

(58) Field of Classification Search
USPC ............. 128/207.14–207.18, 207.29, 201.13; 604/506, 21, 23, 27, 513, 19, 533–539, 604/192, 411
See application file for complete search history.

(56) References Cited

U.S. PATENT DOCUMENTS

| | | |
|---|---|---|
| 4,351,328 A | 9/1982 | Bodai |
| 4,531,328 A | 7/1985 | Jewett |
| D282,772 S | 2/1986 | Fleury |
| 4,569,344 A | 2/1986 | Palmer |
| 4,836,199 A * | 6/1989 | Palmer ..................... 128/207.16 |

(Continued)

FOREIGN PATENT DOCUMENTS

| | | |
|---|---|---|
| WO | 99/29359 | 6/1999 |
| WO | WO9929359 | 6/1999 |

OTHER PUBLICATIONS

International Search Report, Jun. 8, 2005.

*Primary Examiner* — Kevin T Truong
*Assistant Examiner* — Si M Lee
(74) *Attorney, Agent, or Firm* — Knobbe, Martens, Olson & Bear, LLP.

(57) ABSTRACT

A patient ventilating (23) and aspirating system (8) is disclosed that has a suction tube (9) and connector (6) for connecting to a catheter mount that has a scaled passageway (15). The catheter mount passageway (15) is sealed with an elastomeric seal (16) including a perforation or slit (17). A connector (12) with a piercing member is associated with the suction tube (9). When the connector is attached to the catheter mount the piercing member (20) pierces the seal (16) such that the suction tube (9) can pass through the connector (6) and catheter mount.

8 Claims, 7 Drawing Sheets

(56) References Cited

U.S. PATENT DOCUMENTS

| | | | |
|---|---|---|---|
| 5,060,646 A | 10/1991 | Page | |
| 5,135,489 A | 8/1992 | Jepson et al. | |
| 5,255,676 A | 10/1993 | Russo | |
| 5,309,902 A * | 5/1994 | Kee et al. | 128/202.27 |
| 5,329,921 A | 7/1994 | Socaris et al. | |
| 5,501,214 A | 3/1996 | Sabo | |
| 5,513,628 A * | 5/1996 | Coles et al. | 128/200.26 |
| 5,549,554 A | 8/1996 | Miraki | |
| 5,598,840 A * | 2/1997 | Iund et al. | 128/207.14 |
| 5,640,951 A | 6/1997 | Huddart et al. | |
| 5,715,815 A * | 2/1998 | Lorenzen et al. | 128/207.14 |
| 5,775,325 A | 7/1998 | Russo | |
| 5,779,687 A * | 7/1998 | Bell et al. | 604/265 |
| 6,217,568 B1 | 4/2001 | Jepson et al. | |
| 6,245,048 B1 | 6/2001 | Fangrow, Jr. et al. | |
| 6,261,266 B1 | 7/2001 | Jepson et al. | |
| 6,269,813 B1 * | 8/2001 | Fitzgerald et al. | 128/207.16 |
| 6,287,280 B1 * | 9/2001 | Lampropoulos et al. | 604/167.03 |
| D453,221 S | 1/2002 | Haytman et al. | |
| 6,575,944 B1 | 6/2003 | McNary et al. | |
| 6,702,789 B1 | 3/2004 | Hargett et al. | |
| 6,758,833 B2 | 7/2004 | Lopez | |
| 6,769,430 B1 * | 8/2004 | Carlsen et al. | 128/201.13 |
| 6,923,184 B1 * | 8/2005 | Russo | 128/207.14 |
| 7,523,967 B2 | 4/2009 | Steppe | |
| 7,549,419 B2 * | 6/2009 | Carlsen et al. | 128/201.13 |
| 7,665,465 B2 | 2/2010 | Radney | |
| 2001/0044600 A1 * | 11/2001 | Elkins | 604/119 |
| 2002/0087144 A1 | 7/2002 | Zinger et al. | |
| 2004/0007236 A1 | 1/2004 | McGee | |
| 2004/0181192 A1 | 9/2004 | Cuppy | |
| 2004/0255952 A1 * | 12/2004 | Carlsen et al. | 128/207.14 |
| 2006/0025724 A1 | 2/2006 | Chen | |
| 2006/0064065 A1 | 3/2006 | Russo | |
| 2006/0149189 A1 | 7/2006 | Diamond et al. | |
| 2006/0212000 A1 * | 9/2006 | Fangrow, Jr. | 604/247 |
| 2006/0249153 A1 | 11/2006 | DeVries et al. | |
| 2006/0249160 A1 | 11/2006 | Scarberry et al. | |
| 2008/0287906 A1 | 11/2008 | Burkholz et al. | |
| 2009/0182309 A1 | 7/2009 | Muffly | |

* cited by examiner

PATIENT VENTILATING AND ASPIRATING SYSTEM

BACKGROUND OF THE INVENTION

1. Field of the Invention

This invention relates to a catheter tube connector, and in particular, but not solely to a catheter tube connector for a suction system used with a tracheostomy or endrotracheal patient ventilation system.

2. Summary of the Prior Art

There are a number of medical procedures that require placement of a tracheostomy or endotracheal tube into the windpipe to deliver air directly into the lungs. A patient who is ventilated in this manner cannot clear secretions collecting in their lungs and airways by themselves. To overcome this problem, a sterile flexible aspirating tube is inserted into the patient via the tracheostomy or endotracheal tube. The aspirating tube is used in conjunction with an external vacuum source to create suction and help clear the secretions. In the method of secretion removal known as the open suction system, the aspirating tube is disposed of immediately after use as it will have become contaminated by the pathogens and bacteria that live in the patient's airway, and once it is removed from the patient's airway the tube will be exposed to atmosphere, with the risk of contaminating caregivers. An alternative to the open suction system is known as the closed suction system, where the aspirating tube is enclosed within a sealed flexible plastic envelope when outside the patient, allowing the aspirating tube to be used several times and then changed either when necessary or after a set period, usually every 24 hours. The closed suction system provides a degree of protection from contaminants for anyone in contact with the patient, such as caregivers and similarly protects the patient from caregivers and the like. Since it was first introduced, various aspects of the closed system have been refined in order to improve the usefulness of the system.

U.S. Pat. No. 4,351,328 discloses a combined tracheostomy ventilator tube and patient aspirating system of the open type. The device disclosed has the disadvantage that the aspirating catheter tube is exposed to the atmosphere before being pushed into the trachea via the tracheostomy tube. The catheter tube also comes into contact with the external parts of the seal as it penetrates through it, allowing it to pick up germs on the external surfaces of the ventilator before depositing these in the patient's lungs. A further disadvantage of this system is that the resistance of the tube passing through and over the seal can be high, and can cause the patient some discomfort as the tracheostomy tube and other fittings are inadvertently moved and twisted in order to overcome this resistance.

U.S. Pat. No. 4,569,344 discloses a combined tracheostomy ventilator tube and patient aspirating system of the closed type. The device disclosed has the disadvantage that the ventilator tube is unsealed when the connector is released in order to carry out routine cleaning or maintenance, or in order to replace the aspirating system, allowing external airborne germs to enter the trachea through the ventilator tube. Also, it is difficult to maintain PEEP (Positive end-expiratory pressure) within the system if the system is not sealed, such as is the case here when the connector is released. If PEEP is not maintained throughout the system, not only can this affect the ventilation of the patient, but in the most common form of tracheal tube layout, an inflated cuff is used to hold and seal the ventilation and aspiration cannula of the tracheostomy tube in place in the patient's windpipe. If PEEP is lost, this cuff can deflate, allowing subglottic fluids that have pooled above the cuff to leak into the patient's lungs. The device disclosed in this specification also has the disadvantage that the end of the catheter tube is fully exposed before connection, and makes contact with exposed portions of the external surfaces of the ventilator as it is pushed through into the trachea, leading to a greater chance of infecting the patient.

U.S. Pat. No. 5,060,646 discloses a similar closed system for ventilation and aspiration. This system has the disadvantage that the aspirating assembly containing the catheter tube cannot be removed for replacement or maintenance without unsealing the ventilating system, malting it difficult to maintain PEEP, and allowing airborne germs to enter the system. Whilst in this case the catheter tube can be inserted into the ventilator without coming into contact with the external surfaces, this can only occur when the ventilator is unsealed, with the previously mentioned disadvantages. Also, removing and connecting the aspirating assembly is via a resistance fitting, and so the patient can experience discomfort from the increased likelihood of twisting and pulling, as outlined above.

SUMMARY OF THE INVENTION

It is an object of the present invention to provide a ventilating and aspirating apparatus that overcomes one or more of the above mentioned problems or disadvantages, or which at least provides the public with a useful alternative.

In a first aspect the invention consists in a patient ventilating and aspirating system, comprising:

a pressurised source of gases, gases transport means adapted to convey said gases in use to said patient, a patient connector, adapted to deliver said gases to a patient through a tracheostomy or endotracheal tube fitting, said patient connector adapted to be in fluid communication with said gases transport means in use, a catheter mount that is substantially tubular and adapted to be fitted in use between said patient connector said gases transport means, said catheter mount including an additional passageway for receiving an aspirating system, said passageway covered by a seal, said seal including a re-sealing mechanism, and a suction tube, with a distal end and a proximal end, surrounded by a collapsible envelope, said distal end fitted with a distal connector and said proximal end being moveable through a proximal connector attached to said envelope, said distal connector adapted to allow said distal end of said suction tube to be connected to a suction means in use, said proximal connector being releasably connected to said catheter mount, said proximal connector including a piercing member capable of piercing said seal when said proximal connector and said catheter mount are connected, said suction tube capable of passing through said piercing member and not contacting said seal.

In a second aspect the present invention consists in a suction tube and connector for connecting to a catheter mount having a sealed passageway comprising:

a tube, with a distal end and a proximal end, a collapsible envelope surrounding said tube, a distal connector fitted to said distal end and adapted to allow said distal end of said suction tube to be connected to a suction means in use, a proximal connector attached to said envelope that said proximal end of said tube is moveable through, said proximal connector that is releasably connected to said catheter mount, a piercing member that is capable of piercing said seal and said suction tube is capable of passing through said piercing member and not contact said seal.

BRIEF DESCRIPTION OF THE DRAWINGS

Preferred forms of the present invention will now be described with reference to the accompanying drawings.

DETAILED DESCRIPTION OF THE PREFERRED EMBODIMENTS

Figure 1:
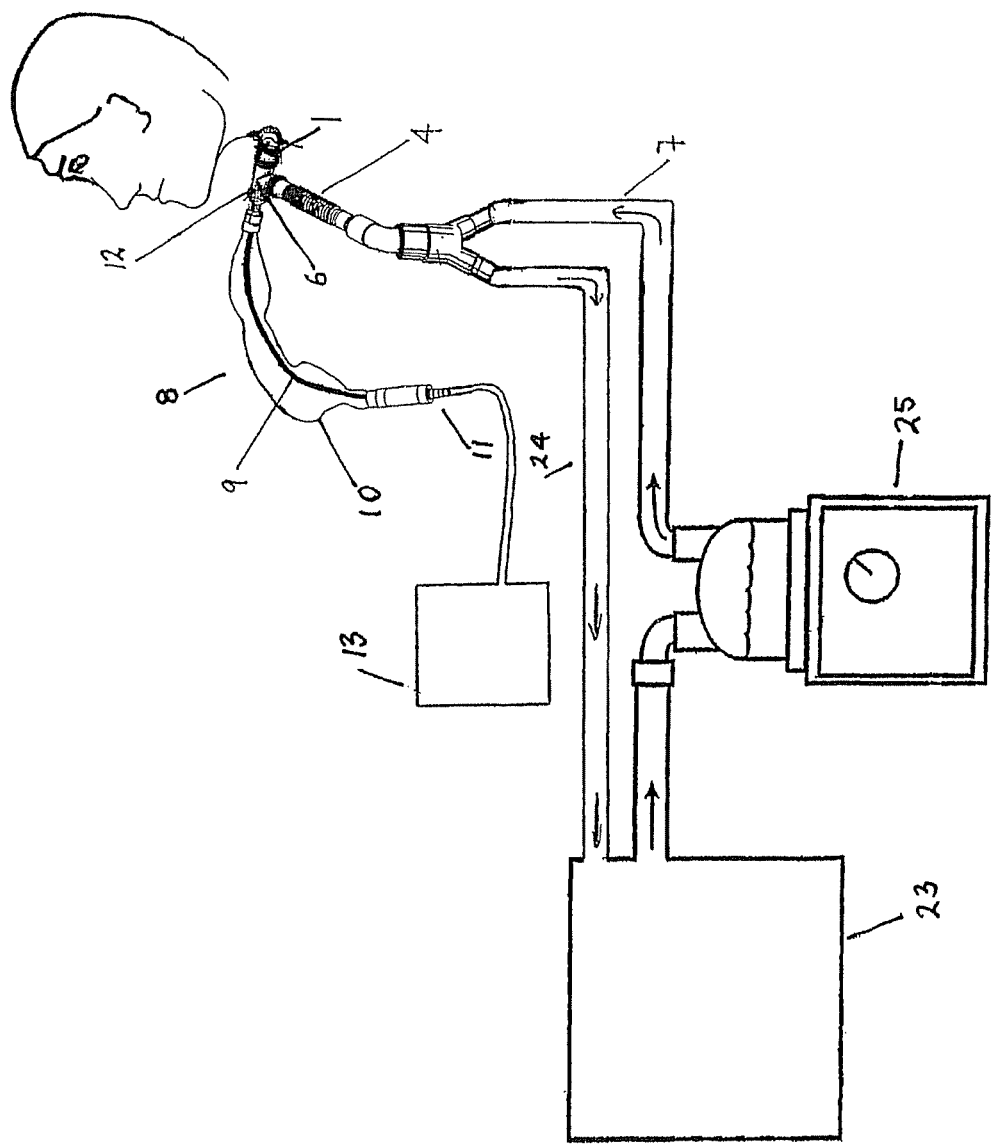
FIG. 1 shows a ventilating circuit in use by a patient, such as might be used with the present invention, in particular an aspirating assembly of the present invention is shown utilising an elbow connector, catheter tube and a tracheostomy or endotracheal connector.

The present invention consists of several separate pieces that are fitted together to form a system to ventilate and aspirate a patient 3. The system comprises a tracheostomy or endotracheal connector 1 (hereinafter "patient connector 1") which in use attaches to the tracheostomy or endotracheal fitting 2 located in the neck or throat of a patient 3. In the Figures the patient is only shown with tracheostomy not an endotracheal fitting and tube. An elbow connector 6 and catheter tube 4 are connected together to form a catheter mount. The elbow connector 6 is attached to the patient connector 1. An aspirating assembly 8 is also provided that is attached to the elbow connector 6. The catheter tube 4 is effectively a piece of tubing that connects the elbow connector 6 to the ventilator system that supplies gases to the patient's airways.

In the preferred embodiment described, the patient has undergone surgery and has had a tracheostomy or endotracheal fitting 2 inserted into his or her tracheostomy in order to allow ventilation and aspiration.

Figure 2:
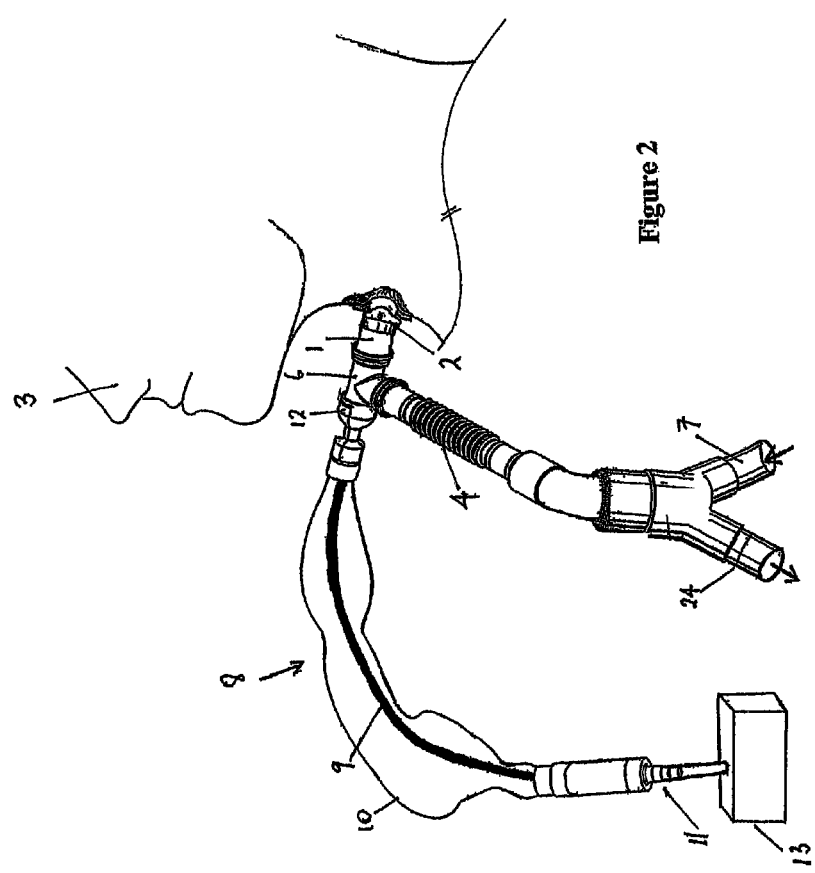
FIG. 2 is a detailed view of the aspirating assembly and the catheter tube and elbow connector of FIG. 1, showing also the patient and a ventilation tube that connects the aspirating assembly to a suction pump.

Referring to FIGS. 1 and 2, a ventilation and humidifying system as might be used with the suction catheter tube connector of the present invention is shown. A patient 3 is receiving humidified and pressurised gases through the tracheostomy or endotracheal fitting 2 (hereinafter "patient fitting 2"). The catheter tube 4 is connected to a humidified gases transportation pathway or inspiratory conduit 7 that in turn is connected to a humidifier 25 supplied with gases from a ventilator 23. An expiratory conduit 24 transports gases from the patient back into the ventilator to assist the breathing of patient 3. The ventilator 23, humidifier 25 and conduit 24 that make up the ventilation and humidifying system are disclosed in the prior art, and may be of the type described in U.S. Pat. No. 5,640,951 to Fisher and Paykel Limited.

The aspirating assembly 8 consists of a suction tube 9, a collapsible and flexible plastic envelope 10 and at least two fittings at each end, in particular, a distal fitting 11 furthest from the patient, and a proximal connector 12 nearest to the patient 3. The suction tube 9 is capable of being slid backwards and forwards through the proximal connector 12, such that in use the envelope 10 collapses and expands back out lengthwise with movement of the suction tube 9. The proximal connector 12 has a releasable connector mechanism allowing attachment to the elbow connector 6 and hence catheter tube 4. The plastic envelope 10 contains any hazardous biological waste from the lungs of the patient 3 that may be deposited on the outside of the suction tube 9. The distal fitting 11 is connected to a suction pump 13. The suction from pump 13 is used to suck fluid from the lungs and airway passages of the patient 3 through the suction tube 9.

Figure 3:
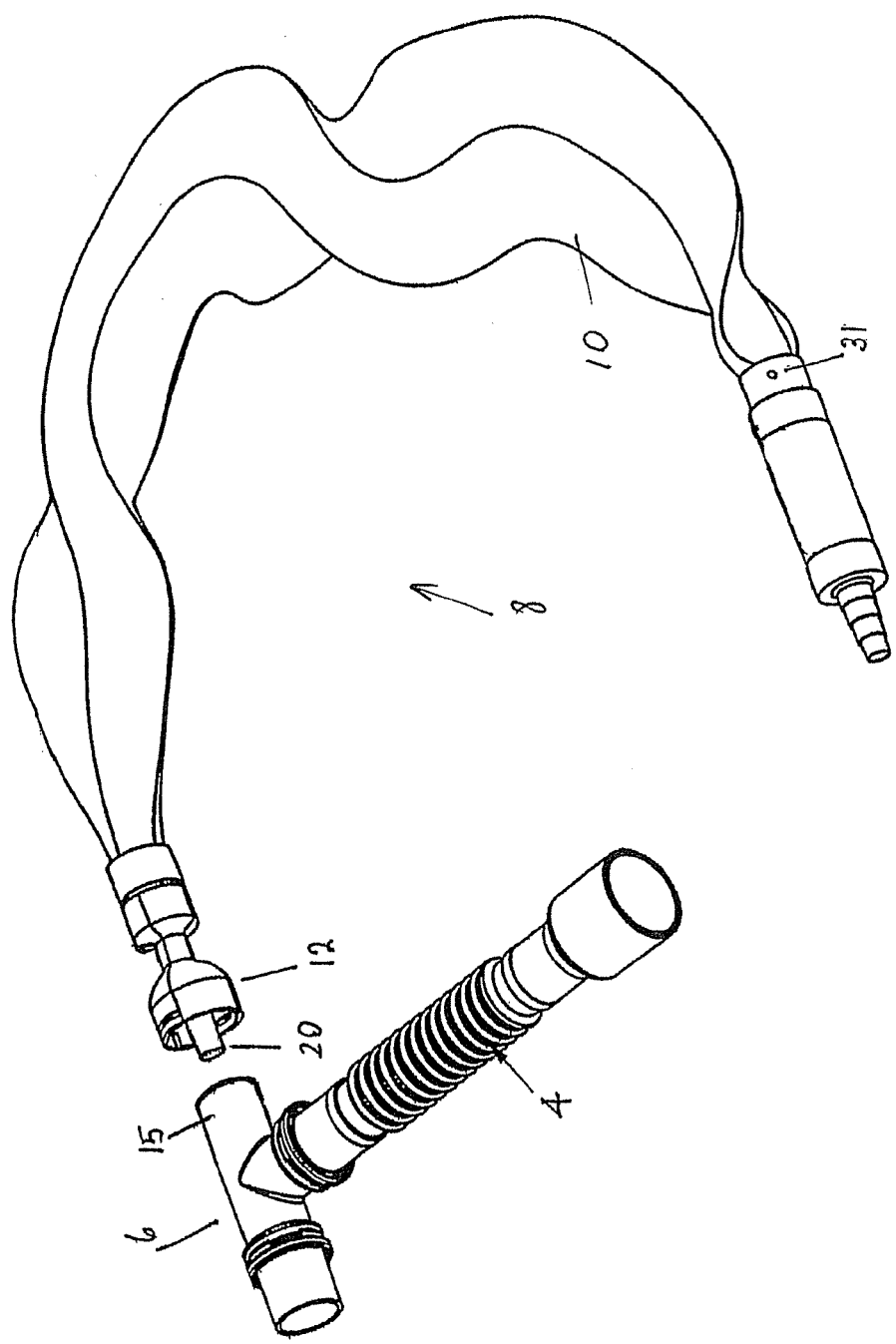
FIG. 3 is a detailed view of the aspirating assembly, showing the catheter tube and elbow connector disconnected from the aspirating assembly.

In order for the suction tube 9 to access the lungs and airways of the patient 3, its length can be pushed through the proximal connector 12, passing through the elbow connector 6, the patient connector 1 and the patient fitting 2 and then into the lungs of the patient 3. In order to prevent obstruction of the patient's airways the suction tube 9 is not left inside the patient 3 when not in use. Thus the suction tube 9 is substantially withdrawn back through the proximal connector 12 and into the plastic envelope 10 when not in use. The plastic envelope 10 is able to collapse around the suction tube 9 as there is a small aperture 31 (see FIG. 3 that enables the venting of air and hence collapse and filling of the envelope with air.

Figure 4:
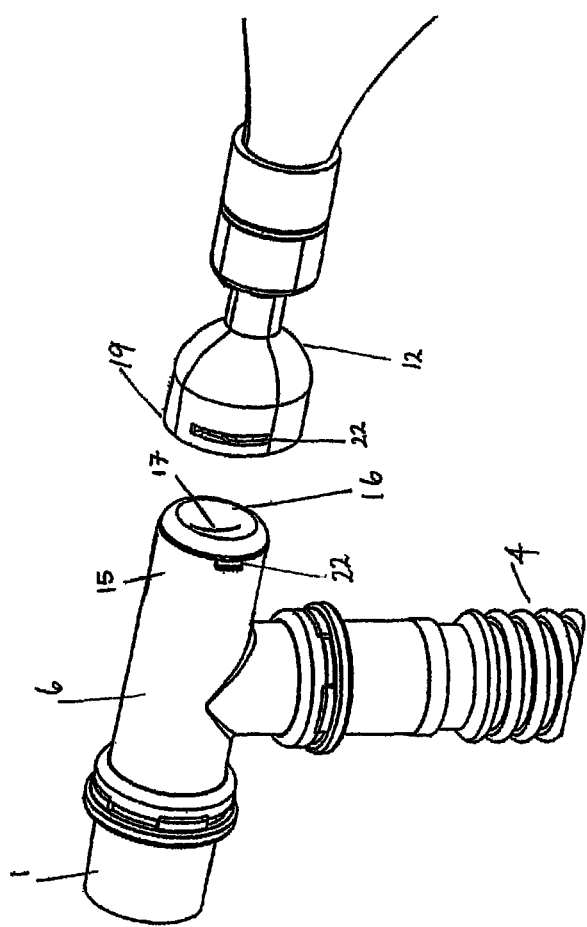
FIG. 4 is a further detailed view of the catheter tube and elbow connector that has an elastomeric seal with a perforation, and a bayonet fitting for connecting the two.

The proximal connector 12 releasably connects the aspirating assembly 8 to the elbow connector 6. In the preferred embodiment shown in FIGS. 3 and 4, the elbow connector 6 and catheter tube 4 are substantially T-shaped in cross-section. The upright of the T-section forms or is connected to the ventilation tube 4. The end of the arm of the T-section forms or is connected to the patient connector 1 and the other end forms a passage 15 which receives the proximal connector 12 of the aspirating assembly 8. A seal 16 is located at the outermost end of passage 15 and seals passage 15. In the preferred embodiment this is an elastomeric material, such as a silicone rubber, and has a slit 17 formed in the centre of the seal. The slit 17 allows the seal 16 to be pierced, for example by a central protrusion 20 (described below) or the suction catheter tube 9, but then to reseal once the object piercing the seal has been removed.

In other forms of the elbow connector and catheter tube an L-shaped configuration may exist where the corner of the L has located within it an aperture in which an elastomeric seal is disposed. In this configuration the passage 15 would be shorter in length.

Figure 5:
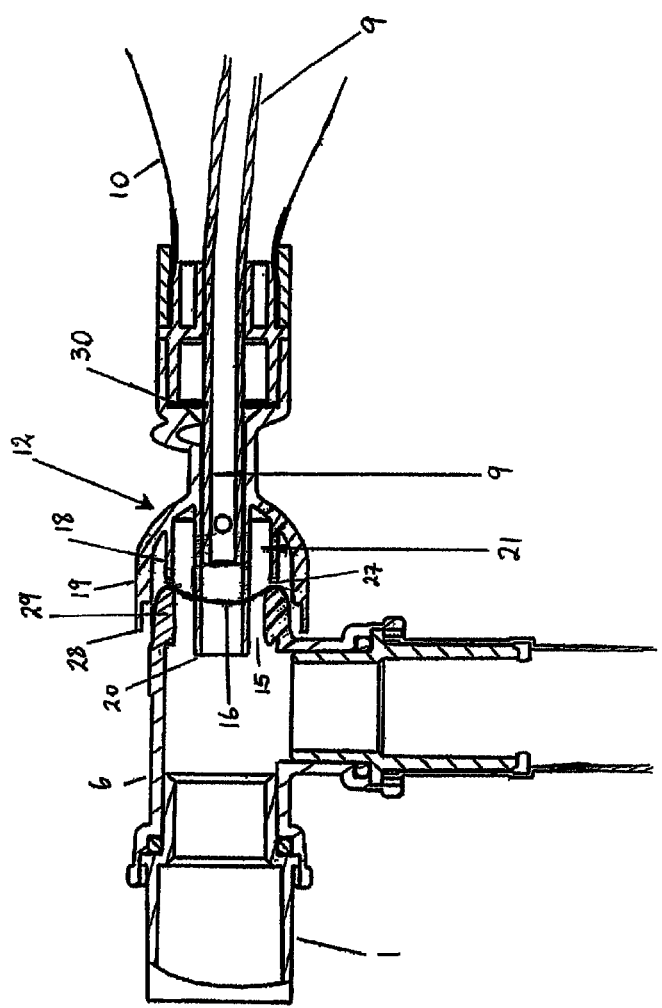
FIG. 5 is a detail cutaway view of the proximal end connector attached to the catheter tube, showing a dead space being created when the aspirating assembly is attached to the catheter tube, and the catheter tube passing through the central protrusion and the seal, and into the catheter tube.

Referring now to FIG. 5, the proximal connector 12 consists of two nested cup-shaped fittings, an inner cup fitting 18 and an outer cup fitting 19, extending around a central protrusion 20. The central protrusion 20 preferably projects past the rim 28 of the outer cup fitting 19, although it is not strictly necessary that the protrusion 20 does. The rim 28 of the outer cup fitting 19 projects past the rim 27 of the inner cup fitting 18. The outer cup fitting 19 preferably has an internal diameter slightly larger than the outer diameter of the elbow connector 6 that forms the passage 15. The inner cup fitting 18 has a diameter slightly smaller than the outer diameter of the crosspiece of the elbow connector 6. The proximal connector 12 and the elbow connector 6 are brought together and connected so that the central protrusion 20 passes through the slit 17 in elastomeric seal 16, and protrudes into the passage 15. The rim of the inner cup fitting 18 abuts the end of the passage 15. A dead space 21 is formed between the outside surface of the seal 16, the inside of the inner cup fitting 18 and the outside surface of the protrusion 20. It is not considered necessary for the seal 16 to be airtight and stop gases escaping to atmosphere when the elbow connector 6 and the aspirating assembly 8 are connected in this matter, as sealing occurs between the seal 16 and the end 27 of the inner cup fitting 18. In any event, any possible leakage that may occur is contained in the dead space 21 formed on connection. The dead space 21 breaks the direct path between gases flowing through the seal 16 and atmosphere as the elbow connector 6 and aspirating assembly 8 are brought together. Once the rim 27 of the inner cup fitting 18 has been pushed against the seal 16 at the end of the passage 15, the rim 27 of the inner cup fitting 18 and seal 16 form a seal that prevents any further leakage to atmosphere.

As the inner cup fitting 18 abuts the seal 16, part of the outer cup fitting 19 overlaps and wraps around the outer end portion 29 of the passage 15. The passage 15 and the outer cup fitting 19 are fitted with a releasable lockable bayonet fitting 22 of the type well known in the prior art. The bayonet fitting 22 prevents inadvertent release of the proximal connector 12 from the elbow connector 6.

In the preferred embodiment, the central protrusion 20 is a hollow tube protruding from the proximal connector 12. The catheter tube 9 fits snugly within the central protrusion 20, and slides easily within it. This snug fit has the advantage that little or no gases escape through the seal 16 to pass between the catheter tube 9 and the central protrusion 20. In the event that gases did escape an additional seal or washer 30 within the proximal connector 12 prevents gases entering the envelope 10. The seal or washer 30 also performs a wiping action about the suction tube and prevents excessive mucus, contaminants and the like to enter the envelope 10.

In some forms of the present invention the envelope 10 may be formed of a breathable material, such as SYMPATEX™.

In use, when the proximal connector 12 and the elbow connector 6 are mated, the protrusion 20 is pushed through the slit 17 in the seal 16 and the proximal connector 12 is locked to the elbow connector 6 using the bayonet fitting 22. The end of the suction tube 9 may then be pushed through the hollow centre of the central protrusion 20 into the elbow connector 6 and then through into the patient connector 1, the patient fitting 2 and into the lungs of the patient 3. After suction operations have been completed, the suction tube 9 may be withdrawn back through the proximal connector 12 and any contaminants on the outside surface of the suction catheter tube 9 are contained safely within the plastic envelope 10.

Once the aspirating assembly 8 and the elbow connector 6 have been mated, there is little or no inadvertent forcing or twisting of the elbow connector and catheter tube 4 in order to push the suction catheter tube 9 through the seal 16. The suction catheter tube 9 moves easily within the tube formed by the central protrusion 20. There is therefore a decrease degree of patient trauma offered by the system of the present invention. The seal 16 and the features of the proximal connector 12 outlined above also ensure that any gas leakage through the seal 16 does not result in an excessive loss of PEEP.

Figure 6:
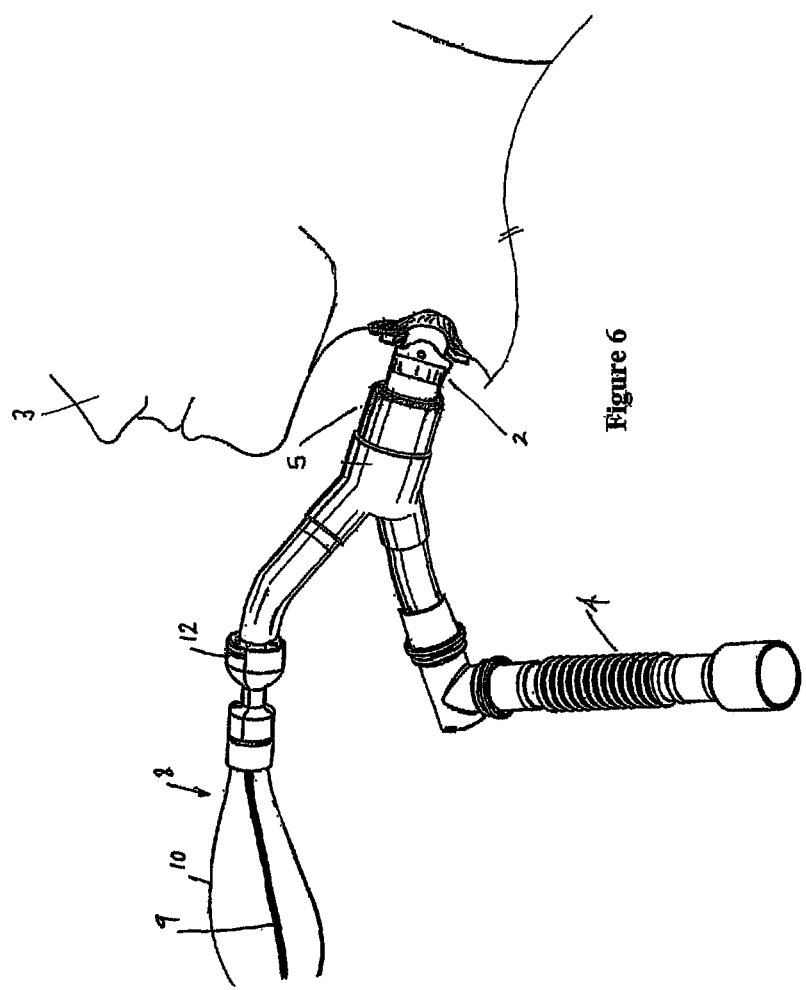
FIG. 6 shows an alternative embodiment of the catheter tube of the present invention, where a bifurcated y-shaped tracheostomy connector is used in place of the catheter tube and tracheostomy connector.

In the preferred embodiment of the present invention described and shown in the figures, the patient connector 1 is connected to, or can be an integral part of, the elbow connector 6. This is a common embodiment for ventilation circuits of this type, although bifurcated y-shaped tracheostomy fittings 5 of the type shown in FIG. 6 that allow an elbow connector 6 and a catheter tube 4 to be separately connected are not unknown.

Figure 7:
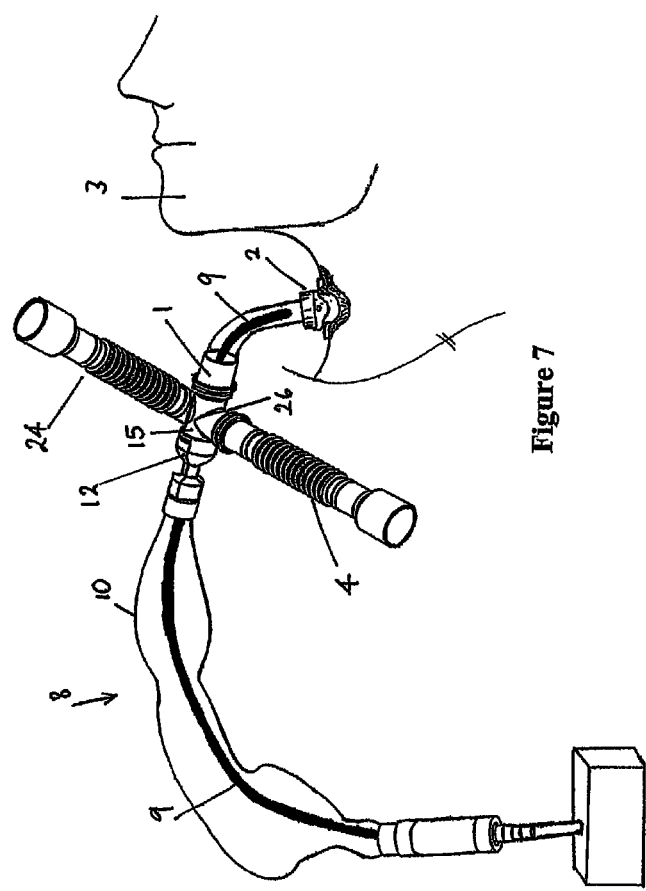
FIG. 7 shows a further alternative embodiment of the catheter tube of the present invention, with a cross- or x-shaped fitting used in place of the T-shaped fitting of the preferred embodiment.

A similar alternative system is shown in FIG. 7 where the aspirating assembly 8 is attached to a cross- or x-shaped catheter tube 26. One branch of the catheter tube 26 forms the passage 15 and the opposing branch forms the patient connector 2. In this embodiment one of the side branches forms the inspiratory conduit 7 and the opposed branch forms either a bleed-off exhalation conduit or expiratory conduit 24 leading back to the ventilator 23 (if being used in an assisted breathing configuration).

Systems of both the types described above in the preferred embodiment and the alternative forms with the bifurcated y-shaped tracheostomy fitting 5, or the x-shaped catheter tube 26, have the advantage that they are modular, and the separate parts, such as the elbow connector 6 or the aspirating assembly 8 can be easily removed from the system and replaced if necessary. This is especially useful, as the aspirating assembly 8 will likely need to be removed and replaced much more frequently that the other parts.

We claim:

1. A patient ventilating and aspirating system, comprising:
   a gases transport conduit adapted to convey pressurized gases in use to a patient,
   a patient connector adapted to deliver said pressurized gases through a tracheostomy or endotracheal tube fitting, said patient connector adapted to be in fluid communication with said gases transport conduit in use,
   a catheter mount that is substantially tubular and adapted to be fitted in use between said patient connector and said gases transport conduit, said catheter mount adapted to convey said pressurized uses from said uses transport conduit to said patient connector and maintain PEEP in the system, said catheter mount including a passageway for receiving an aspirating system, said passageway covered by a seal located on an outer edge of said passageway, said seal including a re-sealing mechanism and configured to provide a substantially airtight seal at normal operating pressures such that said catheter mount is sealed from atmosphere in use, and
   a suction tube, with a distal end and a proximal end, surrounded by a collapsible envelope, said distal end fitted with a distal connector and said proximal end being moveable through a proximal connector attached to said envelope, said distal connector adapted to allow said distal end of said suction tube to be connected to a suction means in use, said proximal connector being releasably connected to said catheter mount with a bayonet fitting, said proximal connector including a piercing member capable of piercing said seal when said proximal connector and said catheter mount are connected, said suction tube capable of passing through said piercing member and not contacting said seal.

2. A patient ventilating and aspirating system according to claim 1 wherein said proximal connector is adapted such that when connected to said catheter mount a chamber is formed, said chamber abutting an outer surface of said seal and an outer surface of said piercing member and creating a dead space therein.

3. A patient ventilating and aspirating system according to claim 2 wherein said proximal connector and said catheter mount are adapted such that when connected, adjacent surfaces on said proximal connector and said catheter mount abut to form a seal and substantially prevent gases leaking into said chamber through said seal from exiting to the atmosphere.

4. A patient ventilating and aspirating system according to claim 1 wherein said seal is made from an elastomeric material.

5. A patient ventilating and aspirating system according to claim 4 wherein said seal includes a perforation, said perforation allowing the piercing of said seal by said piercing member, where said elastomeric material re-seals said passageway once said proximal connector is detached from said catheter mount.

6. A patient ventilating and aspirating system according to claim 2 wherein said chamber and said dead space are shaped in such a manner that gases within said gases transport conduit that may leak through said seal once pierced are enclosed and contained within said dead space.

7. A patient ventilating and aspirating system according to claim 1 wherein said passageway through said catheter mount allows passage of said suction tube there through and entry into said tracheostomy or endotracheal fitting without said suction tube contacting the internal walls of said catheter mount.

8. A patient ventilating and aspirating system according to claim 1 wherein said proximal connector includes a washer to wipe said suction tube upon removal of said suction tube from said catheter mount.

* * * * *